United States Patent
Ritchie et al.

(10) Patent No.: US 6,207,840 B1
(45) Date of Patent: Mar. 27, 2001

(54) PROCESS FOR PREPARING 3-ISOCHROMANONE

(75) Inventors: David John Ritchie; Hannah Sallie Robertson McCann; Jennifer Ann White; Kirstin MacCormick, all of Stirlingshire; Raymond Vincent Heavon Jones, West Lothian; Robin Fieldhouse, Stirlingshire, all of (GB)

(73) Assignee: ZENECA Limited (GB)

( * ) Notice: Subject to any disclaimer, the term of this patent is extended or adjusted under 35 U.S.C. 154(b) by 0 days.

(21) Appl. No.: 09/463,509

(22) PCT Filed: Jul. 28, 1998

(86) PCT No.: PCT/GB98/02250

§ 371 Date: Jan. 24, 2000

§ 102(e) Date: Jan. 24, 2000

(87) PCT Pub. No.: WO99/10335

PCT Pub. Date: Mar. 4, 1999

(30) Foreign Application Priority Data

Aug. 26, 1997 (GB) .................................................. 9718010
Nov. 3, 1997 (GB) .................................................. 9723200

(51) Int. Cl.$^7$ ................................................ C07D 311/04

(52) U.S. Cl. .............................................................. 549/290

(58) Field of Search .......................................... 549/290

(56) References Cited

U.S. PATENT DOCUMENTS

| | | | |
|---|---|---|---|
| 4,424,394 | 1/1984 | Schneider et al. | 560/105 |
| 4,713,484 | 12/1987 | Epstein | 562/406 |
| 5,886,211 | 3/1999 | Hirai et al. | 560/105 |
| 6,002,020 | * 12/1999 | Geissler et al. | 549/290 |
| 6,008,381 | * 12/1999 | Williams et al. | 549/290 |
| 6,075,152 | * 6/2000 | Geissler et al. | 549/290 |

FOREIGN PATENT DOCUMENTS

| | | |
|---|---|---|
| 24 10 782 A1 | 9/1975 | (DE) . |
| 25 26 046 C2 | 1/1976 | (DE) . |

OTHER PUBLICATIONS

Kiji et al., Palladium–Catalyzed, Atmospheric Pressure Carbonylation of Allyic Chlorides in Two–Phase Aqueous Sodium Hydroxide–Organic Solvent Media, Chemistry Letters 957–960 (1988).

Cassar et al., The Use of Phase–Transfer Catalysis in Palladium–Catalyzed Carbonylation of Organic Halides, 121 J. Organometallic Chem. C55–C56 (1976).

Huang & Wu, Palladium (II)–catalysed carbonylation of aromatic halides under conditions of phase transfer catalysis, Chemistry & Industry 548 (1990).

Grushin & Alper, Alkali–Induced Disproportionation of Palladium (II) Tertiary Phosphine Complexes, [L$_2$PdCl$_2$], to LO and Palladium (0). Key Intermediates in the Biphasic Carbonylation of ArX Catalyzed by L$_2$PdCl$_2$, 12 Organometallics 1890–1901 (1993).

Ito et al., Effect of Base on Palladium–Black Catalyzed Carbonylation of Iodobenzene, 48 (7) Bull. Chem. Soc. Japan 2091–2094 (1975).

Bergbreiter et al., New strategies in using macromolecular catalysts in organic synthesis, 74 J. Molecular Catalysis 409–419 (1992).

Kohlpainter & Beller, Palladium–catalyzed carbonylation of benzyl chlorides to phenylacetic acids—a new two–phase process, 116 J. Molecular Catalysis A: Chem. 259–267 (1997).

Cowell & Stille, Synthesis of Lactones by the Palladium-–Catalyzed Carbonylation of Halo Alcohols, 102 (12) J. American Chem. Soc. 4193–4198 (1980).

Sim et al., *Palladium (O) Complex Catalyzed Mono–Carbonylation of Xylylene Dihalides under Phase Transfer Agent (II)*, 9 (3) Bull. Korean Chem. Soc. 185–187 (1988).

Shanyan et al., *Catalysis of Heteronuclear Metal Cluster III. Hydroformylation of 2–Butene*, 1 (2) J. Molecular Catalysis 115–119 (Jun. 1987).

Murahashi et al., *Palladium(0)–Catalyzed Alkoxycarbonylation of Allyl Phosphates and Acetates*, 58 J. Org. Chem. 1538–1545 (1993).

* cited by examiner

Primary Examiner—Deborah C. Lambkin
(74) Attorney, Agent, or Firm—Thomas R. Savitsky

(57) ABSTRACT

3-Isochromanone is prepared by contacting an o-xylene-α, α'-dihalide with carbon monoxide in a two-phase liquid medium, in which one phase is aqueous and the other phase is water-immiscible, in the presence of a catalyst and a hindered amine base.

11 Claims, No Drawings

PROCESS FOR PREPARING 3-ISOCHROMANONE

This appln is a 371 of PCT/GB98/02250 Jul. 28, 1998.

This invention relates to a chemical process and more particularly to a process for preparing 3-isochromanone which is useful in the manufacture of certain agricultural products.

3-Isochromanone is a well known compound and a number of methods for its preparation are described in the chemical literature. In particular, a process is described in WO097/00850 which comprises reacting an o-xylene-α,α'-dihalide derivative with carbon monoxide and water in an organic solvent in the presence of a catalyst and a hydrogen halide capturing agent followed by treatment with an acid. In this process the hydrogen halide capturing agent is preferably an inorganic base. The use of amines in palladium-catalyzed carbonylation reactions are discussed in *J. Org. Chem.* [1993] 58, 1538–45 and in U.S. Pat. No. 4,713,484. These references relate, however, to the alkoxycarbonylation of allylphosphates and acetates and to the preparation of carboxylic acid salts.

Thus, according to the present invention, there is provided an improved process for the preparation of 3-isochromanone which comprises contacting an o-xylene-α,α'-dihalide with carbon monoxide in a two-phase liquid medium, in which one phase is aqueous and the other phase is water-immiscible, in the presence of a catalyst and a hindered amine base.

The o-xylene-α,α'-dihalide starting material has the general formula:

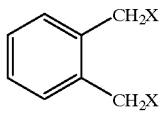

where X is a halogen atom such as chlorine, bromine or iodine, especially chlorine or bromine. o-Xylen-α,α'-dichloride is a particularly convenient starting material.

The process of the invention is carried out in a two-phase liquid medium, one phase comprising water and the other phase conveniently comprising a water-immiscible organic solvent. Any suitable water-immiscible organic solvent may be used. Examples are saturated or aromatic hydrocarbons or halogenated derivatives thereof, such as chlorinated or fluorinated derivatives, for example methylene chloride, toluene or chloro- or fluorobenzene. Xylene is particularly convenient from a manufacturing standpoint. Where the hindered base is a liquid and water-immiscible, it may itself act as the solvent without the need to employ an additional solvent. An example of a base which may be used in this way is N,N-diisopropylethylamine.

It may, however, be convenient to include in the two-phase liquid medium one or more other water-immiscible solvents or a water miscible solvent, provided that at least two-phases are maintained, one of which is aqueous.

Suitably the molar ratio of water:water-immiscible solvent is in the range of 1:50 to 50:1, preferably 1:1 to 10:1 and typically 1:1 to 3:1, for example about 5:2.

There will usually be a molar excess of water used in relation to the quantity of o-xylene-α,α'-dihalide starting material. Preferably the molar ratio of water:o-xylene-α-α'-dihalide will be in the range of 100:1 to 1:1 typically 20:1 to 5:1, for example about 10:1.

The carbon monoxide will normally be dispersed into the two-phase medium either at atmospheric pressure or at pressures up to 100 atmospheres, for example at from 1 to 10 atmospheres. The pressure chosen will depend on the equipment in which the reaction is carried out and the required reaction rates and yield.

Any suitable carbonylation catalyst may be used in the process of the invention, particularly Group VIII (first, second and third triads) metal catalysts, for example palladium, cobalt or iron catalysts. Especially suitable are palladium catalysts, for example palladium (0) and palladium (II) catalysts, which may be water-soluble or water-insoluble, supported on a carrier, such as carbon, silica or calcium carbonate, a polymer or other inert solid, or unsupported. Supported catalysts have the advantage of facilitating catalyst recovery and recycling. Ligands such as triphenylphosphine may be used in conjunction with certain palladium catalysts or it may be beneficial to pre-reduce the catalyst with hydrogen, or another suitable reducing agent.

Suitable water-soluble palladium catalysts in the form of phoshine complexes are described, for example, by J. Kiji et al in *Chem. Lett.*, 957–960 (1988). Suitable water-insoluble palladium catalysts include bis(triphenylphosphine) palladium dichloride and tetrakis(triphenylphosphine) palladium (0) which are described by L. Cassar et al in *J. Organometallic Chem.*, 121 (1976), C55–56, in DE-A-2526046 and by X. Huang et al in *Chem. & Ind.*, Sep. 3, 1990, 548. Palladium (II) catalysed carbonylation reactions are also discussed by V. Grushin et al in *Organometallics*, 12 (5), 1890–1901 (1993). The use of a supported carbonylation catalyst in the form of palladium-black is described by T. Ito et al in *Bull. Chem. Soc. Japan*, 48 (7), 2091–2094 (1975). The use of soluble triphenylphosphine ligands to activate palladium catalysts is described by D. Bergbreiter et al in *J. Mol. Catalysis*, 74 (1992), 409–419. Typical examples of suitable catalysts are palladium chloride, dihydrotetrachloropalladium, tetrakis(triphenylphosphine) palladium (0), dichlorobis(triphenylphosphine)palladium (II), palladium/carbon, palladium on calcium carbonate and palladium on Montmnorillonitel™. Other suitable catalysts and ligands, including water soluble ones, are described in WO 97/00850. The ligands may be used in amounts up to 1000 mole equivalents of palladium, and suitably in the range of from 1 to 200 mole equivalents of palladium. The amount of palladium catalyst used may be in the range of 0.000001 to 0.5 mole equivalents of the o-xylene-α,α'-dihalide.

The hindered amine base will usually be one which has at least two aliphatic, preferably branched aliphatic, or cycloaliphatic groups or one in which the N atom is in a cycloaliphatic or aromatic ring, substituted in a manner that induces steric crowding around the N atom. Typically it will be of low water solubility and have a $pK_a$ of the conjugate acid of about 10. Thus, it may be a heteroaromatic base such as pyridine or a substituted pyridine, for example 2,6-dimethylpyridine. Or it may be a secondary amine, providing it is sufficiently sterically hindered. An example of a suitable secondary amine is 2,2,6,6-tetramethylpiperidine. Preferably, however, it is a tertiary amine of formula $R^1R^2R^3N$ wherein $R^1$, $R^2$ and $R^3$ are independently $C_{1-10}$ alkyl (especially $C_{1-6}$ alkyl) $C_{3-6}$ cycloalkyl, aryl (especially phenyl, but also pyridyl) or aryl($C_{1-4}$)alkyl (especially benzyl), or wherein two or three of $R^1$, $R^2$ and $R^3$ join together with the nitrogen atom to which they are attached to form one, two or three, 5-, 6- or 7-membered alicyclic rings optionally fused and optionally containing a second ring nitrogen atom.

Alkyl groups are straight or branched chain and, unless stated otherwise, contain from 1 to 10, especially from 1 to 6, particularly from 1 to 4, carbon atoms. Examples are methyl, ethyl, iso-propyl, n-propyl, n-butyl, sec-butyl and tert-butyl. Cycloalkyl groups comprise 3 to 6 carbon atoms and are optionally substituted by $C_1$ alkyl. Examples are cyclohexyl, 2-methylcyclohexyl and 2-ethylcyclohexyl.

Suitable tertiary amines of formula $R^1R^2R^3N$ are, for example, N,N-diisopropylethylamine, N,N-dimethylaniline, triethylamine, t-butyldimethylamine, N,N-diisopropylmethylamine, N,N-diisopropylisobutylamine, N,N-diisopropyl-2-ethylbutylamine, tri-n-butylamine, N,N-dicyclohexylmethylamine, N,N-dicyclohexylethylamine, 1,5-diazabicyclo[4.3.0]non-5-ene, 1,4-diazabicyclo[2.2.2]-octane or 2- or 4-dimethylaminopyridine.

There will usually be a molar excess of hindered amine base used in relation to the quantity of o-xylene-α,α'-dihalide starting material. Preferably the molar ratio of amine: o-xylene-α-α'-dihalide will be in the range of 10:1 to 1:1, typically 5:1 to 2:1, for example 4:1 to 2.5:1.

As the process is carried out in a two-phase system, it may be advantageous to include a phase transfer catalyst. By the term "phase transfer catalyst" is meant a substance which, being at least partly present in or wetted by a first (usually organic) phase, promotes reaction between a reactant in the first phase and a reactant which it transfers to the first phase from a second (usually aqueous but sometimes solid) phase. After reaction, the phase transfer catalyst is released for transferring further reactant. Phase transfer catalysts are reviewed by E. V. Dehmlow in *Angewante Chemie* (International Edition), 13 (3), 170 (1974). Other reviews are by Jozef Dockx in *Synthesis* (1973), 441–456 and by C. M. Starks in *JACS.*, (93) 1, Jan. 13, 1971, 195–199.

Suitably the phase transfer catalyst is a quaternary ammonium or phosphonium salt preferably containing bulky organic groups, usually alkyl or aralkyl groups, to make it soluble in the organic phase. It is preferred that the phase catalyst is a tetraalkyl or aralkyl (eg benzyl) trialkyl ammonium or phosphonium salt in which the total number of carbon atoms attached to each nitrogen or phosphorus atom is at least 4. There is little advantage in the number being above 70. It is especially preferred that the number should be in the range of from 16 to 40.

Examples of quaternary ammonium salts are: tetramethylammonium chloride, cetyltrimethylammonium bromide, dicetyldimethylammonium chloride, octyltributylammonium bromide, trioctylmethylammonium chloride (available as Aliquat™ 336), benzyldimethyllaurylammonium chloride, benzyltriethylammonium chloride, dilauryldimethylammonium chloride, tetrabutylammonium bromide and dieicosyldimethylanmmonium chloride. Examples of quaternary phosphonium salts are cetyltripropylphosphonium bromide and triphenylethylphosphonium bromide. Other phase transfer catalysts which may be suitable include crown ethers and polyethylene glycol variants. If used, the phase transfer catalyst may be present in an amount ranging from 0.001 to 0.5 mole equivalents of the o-xylene-α,α'-dihalide.

The process may be carried out at any suitable temperature within a range of from 20° C. to 120° C., preferably from 60° C. to 100° C., typically from 70° C. to 90° C., for example at about 70° C.

After reaction is complete, the reaction mixture is filtered and the aqueous and organic phases separated. 3-Isochromanone in the aqueous phase can be isolated by solvent extraction, for example using dichloromethane, and evaporation of the solvent. 3-Isochromanone in the organic phase can be extracted by the addition of aqueous base to form a salt of the corresponding hydroxy acid. The aqueous layer is separated and the 3-isochromanone regenerated by suitable pH adjustment. Where the palladium catalyst is soluble in the organic phase, the organic layer is retained for recycling and reuse.

When using a palladium catalyst which is soluble in the aqueous phase, the organic phase is separated for isolation of the 3-isochromanone and the aqueous phase is acidified and the palladium catalyst extracted into an organic solvent. The palladium catalyst is recovered for recycling and reuse by extraction of the organic layer with aqueous base. A two-phase carbonylation process of this type using a water-soluble palladium catalyst is described by C Kohlpaintner in *J. Mol. Catalysis A: Chem.* 116 (1997) 259–267.

The use of a supported palladium catalyst has the advantage that it can be filtered from any reaction mixture using known technology, thereby facilitating its recycling and reuse.

3-Isochromanone is useful, inter alia, as an intermediate in the manufacture of agricultural products, especially fungicides of the strobilurin type, for example, those described in EP-A-278595.

The invention is illustrated by the following Examples in which:

| | |
|---|---|
| g = grammes | ml = milliliters |
| mmol = millimoles | ° C. = degrees centigrade |
| M = molar | mp = melting point |
| gc = gas chromatography | rpm = revolution per minute |
| ODCX = o-xylene-α,α'-dichloride | DCM = dichloromethane |
| MR = molar ratio | Wt = weight |
| Act = actual | Str = strength |
| [(CH$_3$)$_2$CH]$_2$NC$_2$H$_5$ = N,N-diisopropyl ethylamine (Hünig's base) | (Ph$_3$P)$_2$PdCl$_2$ = dichlorobis |
| Ph$_3$P = triphenylphosphine | (triphenylphosphine) palladium (II) |

Pressures recorded in 'bar.g' units are gauge measurements, not absolute. Thus, for example, 4 bar.g is equivalent to 5 bar absolute.

EXAMPLES 1 TO 5

The following general procedure was used.

All the listed materials were charged to a 100 ml round-bottom flask and stirred at 650 rpm. A continuous stream of carbon monoxide was bubbled through the reaction mixture whilst heating to 70° C. The reaction mixture was maintained at this temperature and sampled at intervals for analysis of the levels of o-xylene-α,α'-dichloride and 3-isochromanone present.

When the reaction was adjudged complete, the reaction mixture was filtered through a No. 3 sintered glass funnel and the residue washed with xylene (20 ml) and in some cases water (5 ml). The aqueous and organic layers of the filtrate were separated. Water (25 ml) was added to the aqueous layer precipitating a fine white or pink solid. The product was extracted from the aqueous layer with DCM (2×25 ml). Samples of the funnel residue, the organic and aqueous layers and the DCM extract were submitted for quantitative gc analysis.

Example 1 (1% Catalyst, 2.2% Ph₃P)

| Materials | Act Wt(g) | Str (%) | 100% Wt | M Wt | mmol | MR |
|---|---|---|---|---|---|---|
| ODCX | 7.0 | 100 | 7.0 | 175.06 | 39.90 | 1 |
| [(CH₃)₂CH]₂NC₂H₅ | 21.88 | 99 | 21.66 | 129.25 | 167.60 | 4.2 |
| (Ph₃P)₂PdCl₂ | 0.2888 | 97 | 0.2801 | 701.89 | 0.399 | 0.01 |
| Ph₃P | 0.2326 | 99 | 0.2303 | 262.29 | 0.878 | 0.022 |
| H₂O | 7.182 | 100 | 7.182 | 18 | 399.0 | 10 |
| Xylene | 17.29 | 98 | 16.94 | 106.17 | 159.6 | 4 |

Total chemical yield of all detected 3-isochromanone by quantitative gc analysis was 68%.

Example 2 (0.1% Catalyst, 50% Ph₃P)

| Materials | Act Wt(g) | Str (%) | 100% Wt | M Wt | mmol | MR |
|---|---|---|---|---|---|---|
| ODCX | 7.0 | 100 | 7.0 | 175.06 | 39.90 | 1 |
| [(CH₃)₂CH]₂NC₂H₅ | 21.88 | 99 | 21.66 | 129.25 | 167.60 | 4.2 |
| (Ph₃P)₂PdCl₂ | 0.0289 | 97 | 0.0280 | 701.89 | 0.039 | 0.001 |
| Ph₃P | 5.29 | 99 | 5.237 | 262.29 | 20 | 0.5 |
| H₂O | 7.182 | 100 | 7.182 | 18 | 399.0 | 10 |
| Xylene | 17.29 | 98 | 16.94 | 106.17 | 159.6 | 4 |

Total chemical yield of all detected 3-isochromanone by quantitative gc analysis was 51%.

Example 3 (0.1% Catalyst, 10% Ph₃P)

| Materials | Act Wt(g) | Str (%) | 100% Wt | M Wt | mmol | MR |
|---|---|---|---|---|---|---|
| ODCX | 7.0 | 100 | 7.0 | 175.06 | 39.90 | 1 |
| [(CH₃)₂CH]₂NC₂H₅ | 21.88 | 99 | 21.66 | 129.25 | 167.60 | 4.2 |
| (Ph₃P)₂PdCl₂ | 0.0289 | 97 | 0.0280 | 701.89 | 0.039 | 0.001 |
| Ph₃P | 1.057 | 99 | 1.0465 | 262.29 | 100 | 0.1 |
| H₂O | 7.182 | 100 | 7.182 | 18 | 399.0 | 10 |
| Xylene | 17.29 | 98 | 16.94 | 106.17 | 159.6 | 4 |

Total chemical yield of all detected 3-isochromanone by quantitative gc analysis was 37%

Example 4 (0.3% Catalyst, 25% Ph₃P)

| Materials | Act Wt(g) | Str (%) | 100% Wt | M Wt | mmol | MR |
|---|---|---|---|---|---|---|
| ODCX | 7.0 | 100 | 7.0 | 175.06 | 39.90 | 1 |
| [(CH₃)₂CH]₂NC₂H₅ | 21.88 | 99 | 21.66 | 129.25 | 167.60 | 4.2 |
| (Ph₃P)₂PdCl₂ | 0.0866 | 97 | 0.0840 | 701.89 | 0.1197 | 0.003 |
| Ph₃P | 2.58 | 99 | 2.557 | 262.29 | 250 | 0.25 |
| H₂O | 7.182 | 100 | 7.182 | 18 | 399.0 | 10 |
| Xylene | 17.29 | 98 | 16.94 | 106.17 | 159.6 | 4 |

Total chemical yield of all detected 3-isochromanone by quantitative gc analysis was 67%.

Example 5 (Reduced Base Charge)

| Materials | Act Wt(g) | Str (%) | 100% Wt | M Wt | mmol | MR |
|---|---|---|---|---|---|---|
| ODCX | 7.0 | 100 | 7.0 | 175.06 | 39.90 | 1 |
| $[(CH_3)_2CH]_2NC_2H_5$ | 15.63 | 99 | 15.47 | 129.25 | 119.7 | 3.0 |
| $(Ph_3P)_2PdCl_2$ | 0.2888 | 97 | 0.2801 | 701.89 | 0.399 | 0.01 |
| $Ph_3P$ | 0.2326 | 99 | 0.2303 | 262.29 | 0.878 | 0.022 |
| $H_2O$ | 7.182 | 100 | 7.182 | 18 | 399.0 | 10 |
| Xylene | 17.29 | 98 | 16.94 | 106.17 | 159.6 | 4 |

Total chemical yield of all detected 3-isochromanone by quantitative gc analysis was 91%

EXAMPLE 6

To a 100 ml round-bottom flask were charged o-xylene-α,α'-dichloride (7.07 g, 0.0404 moles), N,N-diisopropylethylamine (21.4 g, 0.164 mol), xylene (17.16 g, 0.16 mol), deionised water (7.2 g, 0.4 mol), palladium on Montmorillonite™ catalyst (0.2 g, 0.04 mmol approx) and triphenylphosphine (0.26 g, $9.8\times10^{-4}$ mol). Carbon monoxide was bubbled through the reaction mixture via syringe needle slowly and continuously. The temperature of the reaction mixture was raised to 70° C. and held at 70° C. with vigorous agitation for 30 hours. A sample tested by qualitative gc analysis showed less than 1% area starting material and 51.2% area 3-isochromanone. The reaction mixture was cooled to room temperature and the supported palladium on Montmorillonite™ catalyst was filtered off. The filtrate layers were separated and analysis quantitative by gc analysis showed 36.8% yield 3-isochromanone in the organic layer and 5% yield 3-isochromanone in the aqueous layer.

EXAMPLE 7 o-Xylene-α,α'-dichloride (7.07 g, 0.0404 mol), N,N-diisopropylethylamine (21.4 g, 0.164 mol), palladium on Montmorrilonite™ catalyst (2.0 g, 0.4 mmol approx), xylene (17.16 g, 0.16 mol), deionised water (7.2 g, 0.4 mol) and triphenylphosphine (2.6 g, $9.8\times10^{-3}$ mol) were charged to a 100 ml round bottom flask and carbon monoxide bubbled through via a syringe needle. The reaction mixture was heated to 70° C. while bubbling carbon monoxide through slowly and held at 70° C. for 5 hours. A sample tested by qualitative gc analysis showed less than 1% area starting material and 59.9% area 3-isochromanone. After 20 hours the reaction mixture was cooled to room temperature and the supported palladium on Montmorrilonite™ was filtered off. The filtrate layers were separated and analysed by quantitative gc analysis which showed the organic layer contained 48% yield 3-isochromanone and the aqueous layer contained 11.6% yield 3-isochromanone.

EXAMPLE 8

To a 100 ml round bottom flask were charged, o-Xylene-α,α'-dichloride (7.07 g, 0.0404 mol), N,N-diisopropylethylamine, (21.4 g, 0.164 mol), palladium on Montmorrilonite™ catalyst recycled from Example 7 (2.0 g, 1%) xylene (17.16 g, 0.16 moles) deionised water (7.2 g, 0.4 mol) and triphenylphosphine (2.6 g, $9.8\times10^{-3}$ moles). Carbon monoxide was bubbled through the reaction mixture via a syringe needle and the mixture was heated to 70° C., with slow continuous carbon monoxide bubbling, and vigorous agitation for 20 hours. Qualitative gc analysis showed less than 1% area starting material present and 62% area isochromanone. The reaction mixture was cooled to room temperature and the supported palladium catalyst filtered off. The filtrates were separated into organic and aqueous phases, weighed and submitted for quantitative isochromanone strength by gc analysis. The results showed 47.7% yield of 3-isochromanone in the organic phase and 11.7% yield in the aqueous phase. The Palladium/Montmorrilonite™ M solids filtered off were used in Example 9.

EXAMPLE 9

The procedure used was the same as for Example 8 but using palladium/Montmorrilonite™ catalyst recycled from Example 8. The qualitative gc analysis after 20 hours showed less than 1% area starting material and 44.1% area 3-isochromanone. The organic phase contained 48.6% yield 3-isochromanone and the aqueous phase contained 7.5% yield 3-isochromanone by quantitative gc analysis. The palladium/Montmorillonite™ solids filtered off were used in Example 11.

EXAMPLE 10

The procedure used was the same as for Example 8 but using palladium/Montmorrilonite™ catalyst recycled from Example 9. The qualitative gc analysis after 20 hours showed less than 1% area starting material and 44.7% area 3-isochromanone. The organic phase contained 52.3% yield 3-isochromanone and the aqueous phase contained 9.4% yield 3-isochromanone by quantitative gc analysis.

EXAMPLE 11 o-Xylene α,α'-dichloride (7.10 g, 41 mmol), N,N-diisopropylethylamine (21.40 g, 164 mmol), dichlorobis(triphenylphosphine)palladium (II) (286.3 mg, 0.4 mmol), water (7.2 g, 400 mmol), xylene (20 ml, 160 mmol) and triphenylphosphine (238.4 mg, 0.9 mmol) were charged to a 100 ml three-necked round bottomed flask with stirring. After degassing (×3) under vacuum, a steady flow of carbon monoxide was bubbled through the reaction mixture whilst heating to 70° C. The reaction mixture was maintained at 70° C., with carbon monoxide bubbling through and vigorously stirred (650 rpm) for 24 hours, before sampling for qualitative gas chromatographic analysis. This showed the ratio of 3-isochromanone to starting material to be >99:1 by area percent. The reaction mixture was cooled to ambient temperature, filtered and washed with xylene (10 ml). The filtrates were separated to give an organic solution and an aqueous phase. The total quantitative yield of 3-isochromanone by gc analysis (organic and aqueous phases) was 78.8%.

EXAMPLES 12 TO 21 o-Xylene-α,α'-dichloride (14.0 g, 0.08 mol), N,N-diisopropylethylamine (31.35 g, 0.24 mol) palladium(II) chloride catalyst (0.148 g, 0.8 mmol), o-xylene (34.0 g, 0.32 mol), water (14.4 g, 0.8 mol) and triphenylphosphine (1.0 g, 4.0 mmol) were charged to a 300 ml Inconel™ autoclave. The vessel was then purged with carbon monoxide gas three times (at 5 bar.g) before finally pressurising to approximately 4 bar.g. The contents of the reaction vessel were then briskly agitated (approximately 900 rpm) and heated to 70° C. Once at temperature, the reaction mixture was stirred at 70° C. for 3 to 4 hours, maintaining the pressure at approximately 4 bar.g, and the rate of uptake of carbon monoxide gas was noted. The reaction was adjudged complete approximately when no further carbon monoxide was seen to be consumed. The reaction mixture was then rapidly cooled to below 40° C. and sampled to test for the presence of setting material by gc.

Water (33 g) and sodium hydroxide (27.4 g at 47% strength) were charged in one portion to the open autoclave, which was then sealed and purged with carbon monoxide gas three times (at 5 bar.g) before being finally pressurised to 1 bar.g. The reaction mixture was then stirred at 60° C. under approximately 1 to 2 bar.g (CO pressure) for approximately 1 hour. The reaction mixture was then transferred to a hot separator (in air) and the aqueous and organic phases separated at 60° C. The aqueous phase was drawn off for further work-up by being added cautiously to a stirred solution of xylene and concentrated hydrochloric acid at 60° C. (in air). The mixture was then stirred for 1 hour at 60° C. before being separated to give an a agueous waste stream and a xylene solution containing the product, 3-isochromanone. The xylene solution was recycled by recharging direct to the reaction vessel for use in Example 13.

The same method was used for Examples 13 to 21 except that the ODCX, triphenylphosphine and water were charged to the autoclave containing the organic phase recycled from the previous Example. The only difference between the nine 'recycled' Examples was that additional N,N-diisopropylethylamine base was added in Example 17. Yields of 3-isochloromanone obtained were as follows:

| Example | Yield (%) |
|---------|-----------|
| 12 | 88.7 |
| 13 | 90.7 |
| 14 | 90.3 |
| 15 | 83.5 |
| 16 | 78.4 |
| 17* | 71.6 |
| 18 | 76.4 |
| 19 | 67.2 |
| 20 | 64.0 |
| 21 | 50.8 |

*N,N-diisopropylethylamine (0.08 moles) added at this cycle

EXAMPLE 22 o-Xylene-α,α'-dichloride (14.7 g, 80 mmol), N,N-diisopropylethylamine (31.4 g, 240 mmol), liquid dihydrotetrachloropalladium ($H_2PdCl_4$) catalyst (0.3723 g, 0.8 mmol), o-xylene (34.0 g, 320 mmol), water (14.4 g, 800 mmol) and triphenylphosphine (0.93 g, 4.0 mmol) were charged to a Parr autoclave. The autoclave was purged three times at 5 bar.g with carbon monoxide gas before being finally pressurised to 4 bar.g. The reaction mixture was heated to 70° C. and maintained at this temperature with stirring for 4½ hours. The pressure was maintained at 4 bar.g with carbon monoxide. The reaction was deemed to be complete when no further carbon monoxide was seen to be consumed.

Sodium hydroxide solution (60.3 g at 21 % strength) was charged to a separate jacketed reaction vessel which was evacuated and filled with a carbon monoxide atmosphere. Carbon monoxide was bubbled through the caustic solution while heating to 60° C. The Parr autoclave was evacuated and the solution hydroxide solution charged from the separate jacketed vessel by vacuum displacement. The mixture was stirred for 1 hour at 60° C. and 1 bar.g pressure before separating the organic (63.76 g) and aqueous layers. The aqueous layer was added to a stirred mixture of o-xylene (42.5 g) and concentrated hydrochloric acid (20.3 g at 36% strength). This mixture was stirred at 70° C. for one hour before separating the organic layer (50.72 g xylene solution) and aqueous layer (96.08 g). Analysis of the xylene solution indicated a yield of 76.42% of 3-isochromanone (50.72 g at 17.84 g 3-isochromanone).

What is claimed is:

1. A process for the preparation of 3-isochromanone which comprises contacting an o-xylene-α,α'-dihalide with carbon monoxide in a two-phase liquid medium, in which one phase is aqueous and the other phase is water-immiscible, in the presence of a catalyst and a hindered amine base.

2. A process according to claim 1 in which the o-xylene-α,α'-dihalide is o-xylene-α,α'-dichloride.

3. A process according to claim 1 in which in the two-phase medium, one phase comprises water and the other phase comprises a water-immiscible solvent.

4. A process according to claim 3 in which the molar ratio of water:water-immiscible solvent is in the range of about 1:50 to about 50:1.

5. A process according to claim 3 in which the molar ratio of water:o-xylene-α,α'-dihalide is in the range of about 100:1 to about 1:1.

6. A process according to claim 1 in which the amine base is an amine of formula $R^1R^2R^3N$ wherein $R^1,R^2$ and $R^3$ are independently $C_{1-10}$ alkyl, $C_{3-6}$ cycloalkyl, aryl or aryl($C_{1-4}$)alkyl or wherein two or three of $R^1$, $R^2$ and $R^3$ join together with the nitrogen atom to which they are attached to form one, two or three, 5-, 6- or 7-membered alicyclic rings optionally fused and optionally containing a second ring nitrogen atom.

7. A process according to claim 1 in which the molar ratio of amine base:o-xylene-α,α'-dihalide is in the range of about 10:1 to about 1:1.

8. A process according to claim 1 in which the catalyst is a palladium catalyst.

9. A process according to claim 1 in which the catalyst is present in the amount of about 0.000001 to about 0.5 mole equivalents of the o-xylene-α,α'-dihalide.

10. A process according to claim 1 in which there is present a phase transfer catalyst.

11. A process according to claim 1 which is carried out at a temperature of from about 20° C. to about 200° C.

* * * * *